United States Patent
Jang et al.

(10) Patent No.: US 9,561,081 B2
(45) Date of Patent: Feb. 7, 2017

(54) CONTROL METHODS OF SINGLE-PORT SURGICAL ROBOTS

(71) Applicant: Samsung Electronics Co., Ltd., Suwon-Si, Gyeonggi-Do (KR)

(72) Inventors: Jun Won Jang, Yongin-si (KR); Hyun Do Choi, Yongin-si (KR); Hyung Joo Kim, Seongnam-si (KR); Yo An Lim, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 514 days.

(21) Appl. No.: 14/014,457

(22) Filed: Aug. 30, 2013

(65) Prior Publication Data

US 2014/0257329 A1    Sep. 11, 2014

(30) Foreign Application Priority Data

Mar. 8, 2013 (KR) .................... 10-2013-0025275

(51) Int. Cl.
    *A61B 19/00* (2006.01)
(52) U.S. Cl.
    CPC ........... *A61B 19/2203* (2013.01); *A61B 34/30* (2016.02); *A61B 34/37* (2016.02)
(58) Field of Classification Search
    CPC ............. A61B 19/22; A61B 19/2203; A61B 2019/2207; A61B 2019/2211; A61B 2019/2215; A61B 2019/2219; A61B 2019/2223; A61B 2019/2234
    See application file for complete search history.

(56) References Cited

U.S. PATENT DOCUMENTS

2010/0262162 A1* 10/2010 Omori ............... A61B 19/2203
                                                              606/130
2011/0264113 A1    10/2011 Choi et al.

FOREIGN PATENT DOCUMENTS

| KR | 100778387 B1 | 11/2007 |
| KR | 100994931 B1 | 11/2010 |
| KR | 20110131053 A | 12/2011 |

* cited by examiner

*Primary Examiner* — Todd J Scherbel
(74) *Attorney, Agent, or Firm* — Harness, Dickey & Pierce, P.L.C.

(57) ABSTRACT

A control method of a single-port surgical robot, the single-port surgical robot comprising a slave device including a surgical instrument provided with an elbow and an end effector, and a master device to control motion of the slave device may comprise setting a virtual incision port to an arbitrary position; setting an operating position of the end effector; calculating a target position of the elbow using the set position of the virtual incision port and the set operating position of the end effector; calculating a movement angle of each joint used to move the elbow using the calculated target position of the elbow; and/or calculating a movement angle of each joint used to move the end effector using the calculated target position of the elbow and the set operating position of the end effector.

19 Claims, 10 Drawing Sheets

CONTROL METHODS OF SINGLE-PORT SURGICAL ROBOTS

CROSS-REFERENCE TO RELATED APPLICATION(S)

This application claims priority from Korean Patent Application No. 10-2013-0025275, filed on Mar. 8, 2013, in the Korean Intellectual Property Office (KIPO), the entire contents of which are incorporated herein by reference.

BACKGROUND

1. Field

Some example embodiments may relate to control methods of single-port surgical robots that enable intuitive manipulation like that of multi-port surgical robots.

2. Description of Related Art

Minimally invasive surgery refers to surgical methods to reduce or minimize the size of an incision. Differently from laparotomy using a relatively large surgical incision through a part of a human body (e.g., the abdomen), in minimally invasive surgery, after forming at least one small port (or incision) of 0.5 cm~1.5 cm through the abdominal wall, an operator inserts an endoscope and a variety of surgical instruments through the port, to perform surgery while viewing an image.

As compared to laparotomy, minimally invasive surgery has several advantages, such as reduced need for pain medication before, during, and after surgery, ability to use reduced strength and/or non-addictive pain medications, low pain after surgery, early recovery, early restoration of ability to eat, short hospitalization, rapid return to daily life, and superior cosmetic effects owing to a small incision. Accordingly, minimally invasive surgery has been used in gall resection, prostate cancer, and herniotomy operations, etc., and the use range thereof continues to expand.

In general, a surgical robot used in minimally invasive surgery includes a master device and a slave device. The master device generates a control signal corresponding to doctor manipulation to transmit the control signal to the slave device. The slave device receives the control signal from the master device to perform manipulation required for surgery of a patient. The master device and the slave device may be integrated with each other, or may be separately arranged in an operating room.

Surgical robots and associated systems provide numerous other advantages, such as potentially improved precision, better ability to monitor the patient, and ability to record the surgical procedure for training, qualification, and evidentiary purposes.

Examples of surgical robots include a multi-port surgical robot that forms a plurality of incisions in the body of a patient to insert a plurality of surgical instruments through the respective incisions in a one-to-one ratio, and a single-port surgical robot that forms a single incision in the body of the patient to insert a plurality of surgical instruments through the single incision at once. Here, the single-port surgical robot forms a single incision differently from the multi-port surgical robot and has been in the limelight owing to advantages of the narrow incision and early recovery.

However, since a plurality of surgical instruments is inserted through a single incision to perform surgery, single-port surgery is more limited as to movement of the surgical instruments as compared to multi-port surgery. That is, a single-port surgical robot may be controlled to move only within a conical workspace, an apex of which is a virtual incision center (that may or may not be predetermined). The virtual incision center is referred to as "Remote Center of Motion (RCM)". Under coincidence of the remote center of motion and the patient's incision, surgical instruments inserted into the patient's body are moved only within the conical workspace even if movement occurs at robot arms located outside the incision, which may prevent the incision into which the surgical instrument has been inserted from being damaged due to movement of the robot arms.

During surgery using a plurality of surgical instruments inserted through a single incision, shafts of the surgical instruments may need joint functions like the wrist or elbow such that end effectors of the respective surgical instruments are oriented toward a specific surgical region without a risk of collision therebetween to assist an operator in manipulating the end effectors as if the operator were performing surgery by hand.

SUMMARY

Some example embodiments may provide control methods of single-port surgical robots that enable intuitive manipulation like that of a multi-port surgical robot.

In some example embodiments, a control method of a single-port surgical robot, the single-port surgical robot comprising a slave device including a surgical instrument provided with an elbow and an end effector, and a master device to control motion of the slave device may comprise setting a virtual incision port to an arbitrary position; setting an operating position of the end effector; calculating a target position of the elbow using the set position of the virtual incision port and the set operating position of the end effector; calculating a movement angle of each joint used to move the elbow using the calculated target position of the elbow; and/or calculating a movement angle of each joint used to move the end effector using the calculated target position of the elbow and the set operating position of the end effector.

In some example embodiments, the calculating of the target position of the elbow may be implemented in such a way that the target position of the elbow is positioned in a straight line that connects the position of the virtual incision port and the set operating position of the end effector to each other.

In some example embodiments, the calculating of the target position of the elbow may be implemented using the following equations:

$$\vec{RE} = \vec{RW} + \vec{WE}$$

$$\vec{WE} = \frac{\vec{RV} - \vec{RW}}{|\vec{RV} - \vec{RW}|}|\vec{WE}|$$

In the equations, 'R' denotes a real incision port position, 'V' denotes a virtual incision port position, 'E' denotes an elbow target position, and 'W' denotes an end effector operating position.

In some example embodiments, the setting of the operating position of the end effector may be implemented upon receiving a control signal from the master device.

In some example embodiments, the setting of the position of the virtual incision port may be implemented in such a way that the position of the virtual incision port is located at a surface of a body of a patient, outside the body of the patient, or inside the body of the patient.

In some example embodiments, the method may further comprise, after the calculating of the movement angle of each joint used to move the elbow, judging whether or not the calculated movement angle of each joint is valid.

In some example embodiments, judgment of whether or not the movement angle of each joint is valid may be implemented by judging whether or not the movement angle of each joint is included within a movable angular range of the corresponding joint.

In some example embodiments, after judgment of whether or not the movement angle of each joint is valid, the calculating of the movement angle of each joint used to move the end effector using the calculated target position of the elbow and the operating position of the end effector may be implemented if the movement angle of each joint is valid.

In some example embodiments, the method may further comprise, after judgment of whether or not the movement angle of each joint is valid: searching for another reachable target position of the elbow with respect to the set operating position of the end effector if the movement angle of each joint is not valid; recalculating the movement angle of each joint used to move the elbow using the searched target position of the elbow; and/or judging whether or not the recalculated movement angle of each joint is valid.

In some example embodiments, the searching for the another reachable target position of the elbow may be implemented using a set of all points included in a surface of a sphere about the set operating position of the end effector, a radius of the sphere being a length from the end effector to the elbow.

In some example embodiments, the searching for the another reachable target position of the elbow may be implemented using a three-dimensional (3D) look-up table in which a valid target position of the elbow, among reachable target positions of the elbow with respect to the set operating position of the end effector, is matched to a corresponding operating position of the end effector.

In some example embodiments, the method may further comprise, after the judging of whether or not the recalculated movement angle of each joint is valid, setting the virtual incision port to a new position using the searched target position of the elbow and the set operating position of the end effector if the recalculated movement angle of each joint is valid.

In some example embodiments, after the setting of the new position of the virtual incision port, calculating of the target position of the elbow using the newly set position of the virtual incision port and the set operating position of the end effector may be implemented.

In some example embodiments, the setting of the position of the virtual incision port may be implemented using the following equations:

$$\overrightarrow{RV} = \overrightarrow{RW} + \overrightarrow{WV}$$

$$\overrightarrow{WV} = \frac{\overrightarrow{RE} - \overrightarrow{RW}}{|\overrightarrow{RE} - \overrightarrow{RW}|}(|\overrightarrow{WE}| + |\overrightarrow{EV}|)$$

In the equations, 'R' denotes a real incision port position, 'V' denotes a virtual incision port position, 'E' denotes an elbow target position, and 'W' denotes an end effector operating position.

In some example embodiments, after the judging of whether or not the recalculated movement angle of each joint is valid, searching for the another reachable target position of the elbow and the recalculating of the movement angle of each joint used to move the elbow using the another reachable target position of the elbow are repeatedly implemented if the recalculated movement angle of each joint is not valid.

In some example embodiments, the method may further comprise, after the calculating of the movement angle of each joint used to move the end effector, judging whether or not the calculated movement angle of each joint is valid.

In some example embodiments, after the judging of whether or not the movement angle of each joint is valid, searching for another reachable target position of the elbow with respect to the set operating position of the end effector, recalculating of the movement angle of each joint used to move the elbow using the searched target position of the elbow, and the judging of whether or not the recalculated movement angle of each joint is valid may be repeatedly implemented if the movement angle of each joint is not valid.

In some example embodiments, the searching for the another reachable target position of the elbow may be implemented using a set of all points included in a surface of a sphere about the set operating position of the end effector, a radius of the sphere being a length from the end effector to the elbow.

In some example embodiments, after the judging of whether or not the recalculated movement angle of each joint is valid, setting of a new position of the virtual incision port using the searched target position of the elbow and the set operating position of the end effector may be implemented if the recalculated movement angle of each joint is valid.

In some example embodiments, after the judging of whether or not the recalculated movement angle of each joint is valid, the searching for the another reachable target position of the elbow and recalculation of the movement angle of each joint used to move the elbow using the searched target position of the elbow may be repeatedly implemented if the recalculated movement angle of each joint is not valid.

In some example embodiments, a control method of a single-port surgical robot, the single-port surgical robot comprising a plurality of joints and a surgical instrument provided with an elbow and an end effector, the elbow associated with a target position, and the end effector associated with an operating position may comprise setting a virtual incision port to an arbitrary position; setting the operating position; calculating the target position using the arbitrary position and the operating position; calculating a movement angle of each joint of the plurality of joints used to move the elbow to the target position; and/or calculating a movement angle of each joint of the plurality of joints used to move the end effector to the operating position.

In some example embodiments, the calculating of the movement angle of each joint of the plurality of joints used to move the elbow to the target position may be based on the calculated target position.

In some example embodiments, the calculating of the movement angle of each joint of the plurality of joints used to move the end effector to the operating position may be based on the calculated target position and the operating position.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
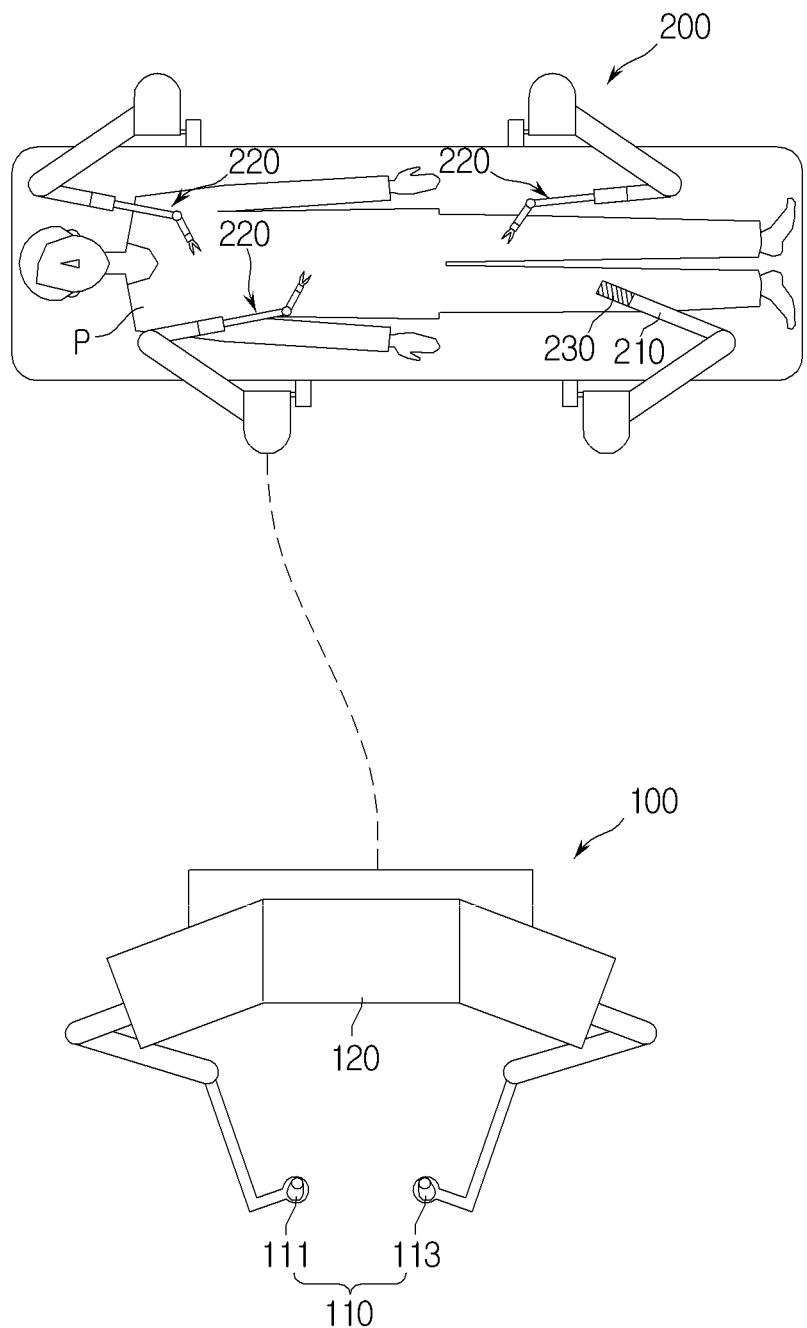
FIG. 1 is a view showing a configuration of a single-port surgical robot.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature, their shapes are not intended to illustrate the actual shape of a region of a device, and their shapes are not intended to limit the scope of the example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

The disclosure may be applied to a single-port surgical robot, without being in any way limited thereto. The single-port surgical robot is configured to perform surgery by inserting a plurality of surgical instruments into the abdominal cavity of the patient through a single incision. The single-port surgical robot may be significantly different than a multi-port surgical robot that forms a plurality of incisions and inserts one surgical instrument through each incision.

Figure 2:
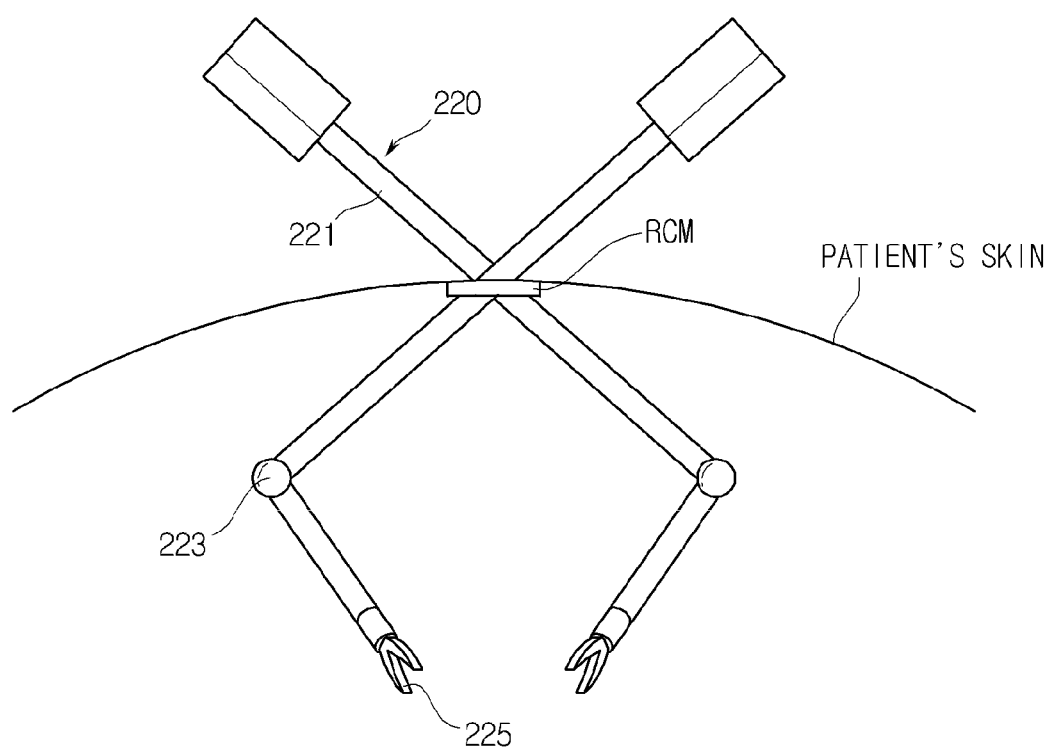
FIG. 2 is a view showing a state in which surgical instruments of the single-port surgical robot are inserted into a patient's body.

FIG. 1 is a view showing a configuration of a single-port surgical robot, and FIG. 2 is a view showing a state in which surgical instruments of the single-port surgical robot are inserted into the patient's body.

Referring to FIG. 1, the single-port surgical robot may basically include a slave device 200 to perform surgery on a patient P who lies on an operating table, and a master device 100 to assist an operator (e.g., a doctor) in remotely controlling the slave device 200. In this case, at least one assistant who assists the operator may be located near the patient P. The doctor may be in the same room, in a different room, or in a different facility (perhaps located in another country).

Here, assisting the operator may mean assisting surgery by the operator in a real space where the patient P is located. This assistance may include a change of used surgical instruments, without being in any way limited thereto. For example, various surgical instruments may be used according to the kind of surgery and the number of robot arms 210 of the slave device 200, and consequently the number of surgical instruments 220 used at once may be limited. In addition, since there is a single incision, the number of surgical instruments 220 to be inserted into the abdominal cavity of the patient P may be limited.

Accordingly, to change surgical instruments during surgery, the operator may instruct an assistant near the patient P to change surgical instruments, and the assistant may change surgical instruments according to the operator's instruction by pulling out the surgical instruments inserted in the abdominal cavity of the patient P to replace the used surgical instruments and inserting other surgical instruments. In this way, surgical instruments may be cleaned, repaired, replaced, etc. during the surgical procedure.

The master device 100 and the slave device 200 may be physically separate devices, without being in any way limited thereto. In one example, the master device 100 and the slave device 200 may be integrated with each other.

As exemplarily shown in FIG. 1, the master device 100 may include an input unit 110 and a display unit 120.

The input unit 110 may receive an instruction input by the operator, such as, for example, an instruction for selection of an operation mode of the surgical robot, or an instruction for remote control of motion of robot arms 210, surgical instruments 220, and an image capture unit 230 of the slave device 200. The input unit 110 according to some example embodiments may include a haptic device, clutch pedal, switch, button, or the like, without being in any way limited thereto. In one example, a voice recognition device may be used. It will be clearly understood that the haptic device will be described hereinafter as one example of the input unit 110, but this is one embodiment and the aforementioned various other devices may be used as the input unit 110.

Although FIG. 1 shows the input unit 110 as including two handles 111 and 113, example embodiments are not limited thereto. For example, the input unit 110 may include one handle, or three or more handles. Multiple handles may facilitate surgical procedures by more than one doctor simultaneously.

The operator may control motion of the robot arms 210 of the slave device 200 by moving the two handles 111 and 113 with both hands. That is, if the operator manipulates the input unit 110, a controller (not shown) may generate a control signal corresponding to information regarding the state of the manipulated input unit 110 using a control signal generator (not shown), and may transmit the control signal to the slave device 200 via a communication unit (not shown).

The display unit 120 of the master device 100 may display, e.g., a three-dimensional (3D) image generated using medical images of the patient before surgery as well as a real image of the interior of the patient's body collected via the image capture unit 230. To this end, the master device 100 may include an image processor (not shown) that receives and processes image data transmitted from the slave device 200 to output the processed data to the display unit 120. As described above, the "image data" may include a 3D image generated using medical images of the patient before surgery as well as a real image collected via the image capture unit 230, without being in any way limited thereto. Advanced processing may allow, for example, combination of data from the medical and real images to improve the quality of visual presentation for the doctor.

The display unit 120 may include one or more monitors such that the respective monitors individually display information required for surgery. In one example, if the display unit 120 includes three monitors, one of the monitors may display, e.g., a real image collected via the image capture unit 230 and a 3D image generated using medical images of the patient before surgery, and the other two monitors may respectively display, e.g., information regarding motion of the slave device 200 and patient information. In another example, a plurality of monitors may display the same image. In this case, the respective monitors may display the same image, or a single image may be displayed on all of the plurality of monitors. In addition, the number of monitors may be determined in various ways according to the type or kind of information to be displayed. For example, the monitors may support stereoscopic viewing or viewing from multiple angles at the same time. The aforementioned display unit 120, for example, may be a Liquid Crystal Display (LCD) unit or a Light Emitting Diode (LED) unit, without being in any way limited thereto.

Here, "patient information" may be information regarding the state of the patient, for example, patient vital signs, such as body-temperature, pulse, respiration-rate, blood-pressure, allergies, medical history, etc. To provide the master device 100 with the vital signs, the slave device 200 that will be described hereinafter may further include a vital sign measurement unit including a body-temperature measurement module, a pulse measurement module, a respiration-rate measurement module, a blood-pressure measurement module, etc. To this end, the master device 100 may further include a signal processor (not shown) that receives and processes information transmitted from the slave device 200 to output the processed information to the display unit 120.

The slave device 200 may include a plurality of robot arms 210, and surgical instruments 220 mounted at ends of the respective robot arms 210. In this case, although not shown in FIG. 1, a body (not shown) to which the plurality of robot arms 210 is coupled may be provided. The body (not shown) may be configured to fix and support the plurality of robot arms 210.

Although not shown in detail in FIG. 1, each of the plurality of robot arms 210 may include a plurality of links and a plurality of joints. Each joint may serve to connect two links to each other, and may have 1 degree of freedom (DOF) or more. The DOF refers to a DOF with regard to kinematics or inverse kinematics. The DOF of a mechanism refers to the number of independent motions of the mechanism, or the number of variables that determine independent motions at relative positions between links. For example, an object in a 3D space defined by X-, Y-, and Z-axes has 3 DOF to determine a spatial position of the object (a position on each axis) and/or 3 DOF to determine a spatial orientation of the object (a rotation angle relative to each axis). More specifically, it will be appreciated that an object has 6 DOF if the object is movable along each of X-, Y-, and Z-axes and is rotatable about each of X-, Y-, and Z-axes.

Figure 3:
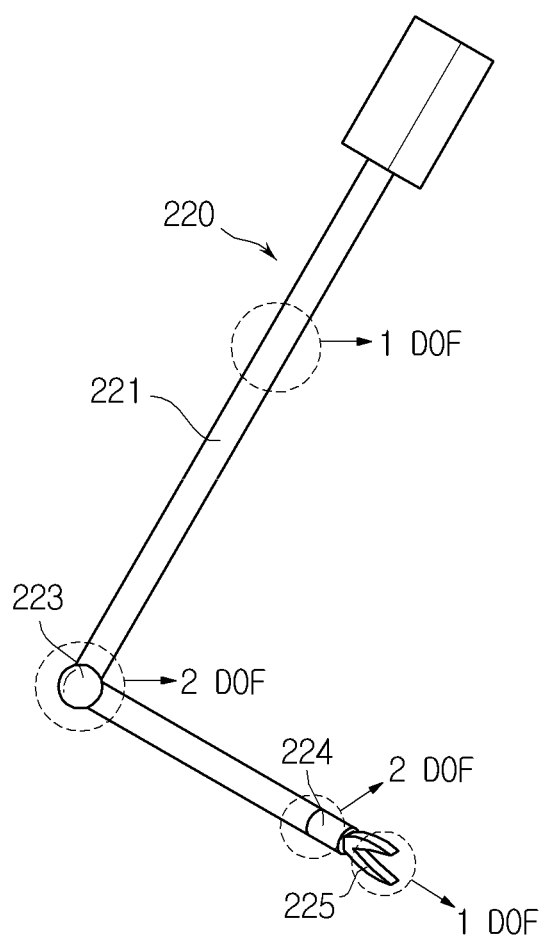
FIG. 3 is a view showing the degree of freedom (DOF) of each part of the surgical instrument of the single-port surgical robot.

As exemplarily shown in FIG. 3, the surgical instrument 220 according to some example embodiments may include a shaft 221 and an end effector 225 coupled to a distal end of the shaft 221.

The shaft 221 linearly extends in a given direction and typically takes the form of a cylindrical tubular member. Pulley wires connected to respective parts of the end effector 225 are received in the shaft 221 to transmit drive power to the end effector 225 in response to a control signal input by the operator. As such, if the control signal generated by manipulation of the operator is received, the received control signal may be transmitted to the respective parts of the end effector 225 through the pulley wires, enabling the end effector 225 to perform motion.

The shaft 221 of the surgical instrument 220 according to some example embodiments, as exemplarily shown in FIG. 3, may include an elbow 223 at a middle position thereof. The elbow 223 assists the shaft 221 in the form of a linear member in bending by a desired angle (that may or may not be predetermined).

Differently from a multi-port surgical robot, the single-port surgical robot performs surgery by inserting all of the plurality of surgical instruments 220 and the image capture unit 230 through a single incision as exemplarily shown in FIG. 2. Therefore, when using linear surgical instruments as in the multi-port surgical robot, it may be difficult to manipulate the surgical instruments 220 such that all of the end effectors 225 thereof are oriented toward a specific surgical region. Accordingly, as exemplarily shown in FIG. 3, the surgical instrument 220 including the shaft 221 provided with the elbow 223 may be provided such that the end effector 225 coupled to the distal end of the shaft 221 may be easily oriented toward a specific surgical region as the shaft 221 is bent about the elbow 223.

In addition, the surgical instrument 220 according to some example embodiments may operate as a mechanism having 6 DOF as exemplarily shown in FIG. 3, without being in any way limited thereto. For example, in the case of the surgical instrument 220 in which the end effector 225 serves as a gripper, the shaft 221 may operate as a mechanism having a total of 6 DOF in such a way that the shaft 221 has 1 DOF to rotate in a roll direction, the elbow 223 has 2 DOF to rotate in a pitch direction and a roll direction, a wrist 224 has 2 DOF to rotate in a yaw direction and a pitch direction or to rotate in a pitch direction and a roll direction, and the end effector 225 has 1 DOF for gripping.

The end effector 225 is a part of the surgical instrument 220 that practically acts on a surgical region of the patient P. For example, the end effector 225 may include a clamp, grasper, scissors, skin holder, staple applier, needle holder, scalpel, cutting blade, or the like, without being in any way limited thereto. Any other known instruments required for surgery may be used.

The single-port surgical robot according to some example embodiments may include five joints each having 1 DOF to determine an operating position of the end effector 225, without being in any way limited thereto. Here, the "five joints each having 1 DOF" may include three joints each having 1 DOF to determine positions of the elbow 223 and the end effector 225 in X, Y, and Z coordinates, and two joints each having 1 DOF to determine an operating position of the end effector 225. In this case, 2 DOF required to determine an operating position of the end effector 225 may correspond to selectively applicable redundancy.

Figure 4:
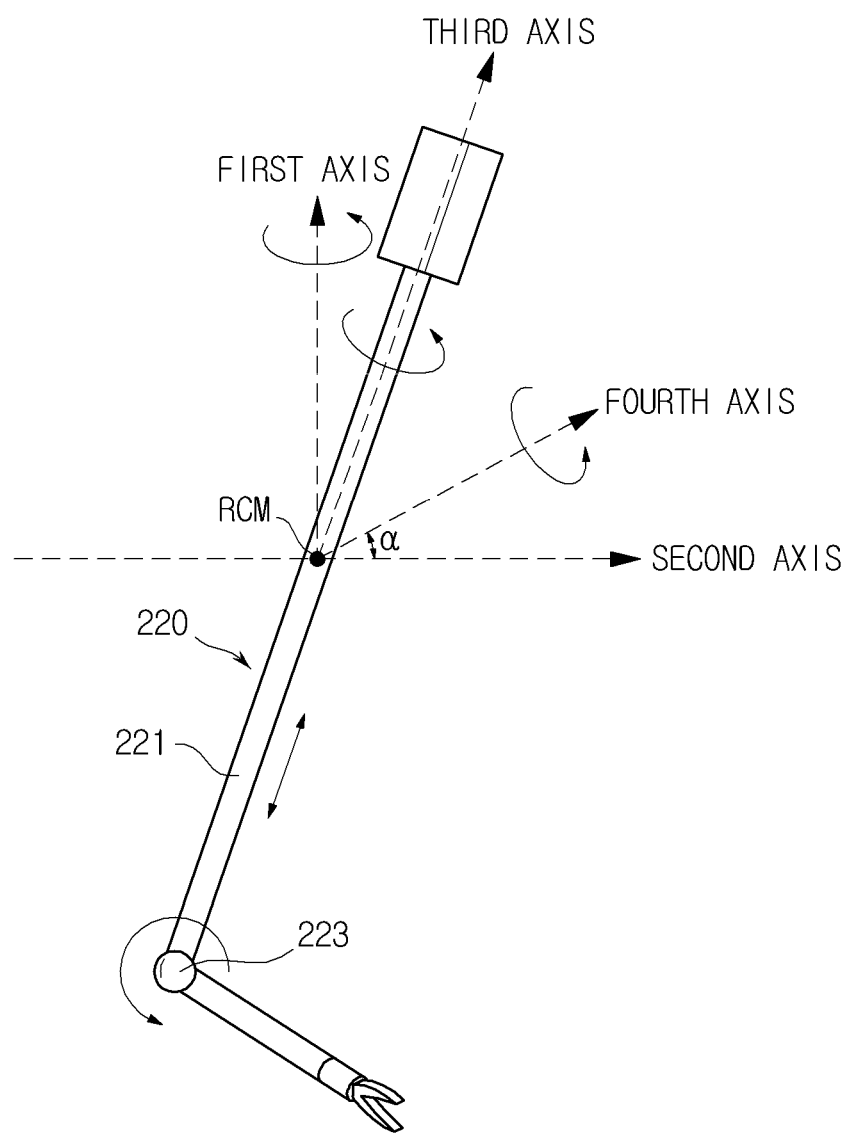
FIG. 4 is a view showing a robot arm having 5 DOF.

More specifically, as exemplarily shown in FIG. 4, the robot arm 210 equipped with the surgical instrument 220 may include five joints each having 1 DOF, including a first joint to rotate about a first axis that vertically penetrates a Remote Center of Motion (RCM), a second joint to rotate about a fourth axis displaced by an angle α from a second axis perpendicular to the first axis, a third joint to linearly move in a direction parallel to a third axis that is the center axis of the shaft 221 of the surgical instrument 220, a fourth joint to rotate about the third axis, and a fifth joint to rotate about the elbow 223 as a reference zero point.

That is, in some example embodiments, the elbow 223 may be moved to a target position based on calculated movement angles of the first, second, and third joints, and the end effector 225 may be moved to an operating position based on calculated movement angles of the fourth and fifth joints.

During surgery using the single-port surgical robot, the operator remotely controls motion of the end effector 225 of the surgical robot. In this case, to allow the end effector 225 to perform motion according to manipulation of the operator, it may be necessary for the surgical robot to drive a plurality of joints. That is, if information regarding an operating position of the end effector 225 that the operator desires is transmitted via manipulation, the surgical robot may calculate a movement angle of each joint with regard to the transmitted position and move the joint based on the calculated movement angle. As a result, the end effector 225 may be moved to the desired operating position. Such calculation of the movement angle of the joint corresponding to given position information is referred to as inverse kinematics.

In general, calculation of the movement angle of each joint is performed via computation of the Jacobian matrix or via morphological analysis of the surgical robot. The former method suggests a general solution frame, but causes error accumulation and is not optimized to a corresponding robot. The latter method does not suggest a general solution frame, but acquires a solution optimized to a corresponding robot. Some example embodiments may provide methods to effectively control the end effector 225 via analysis of mechanical properties of the robot and application of inverse kinematics. To this end, in some example embodiments, a virtual incision port that is not present in reality is set to a position and the elbow 223 is positioned on a straight line that connects the set position of the virtual incision port and an operating position of the end effector 225 to each other, which realizes a surgical instrument that is bent in reality, but enables intuitive manipulation like a straight surgical instrument. This approach provides significant advantages to the doctor, such as ease of learning to manipulate the surgical robot, improved ability to anticipate how the doctor's movements will translate into movements of the surgical robot, etc.

Figure 5:
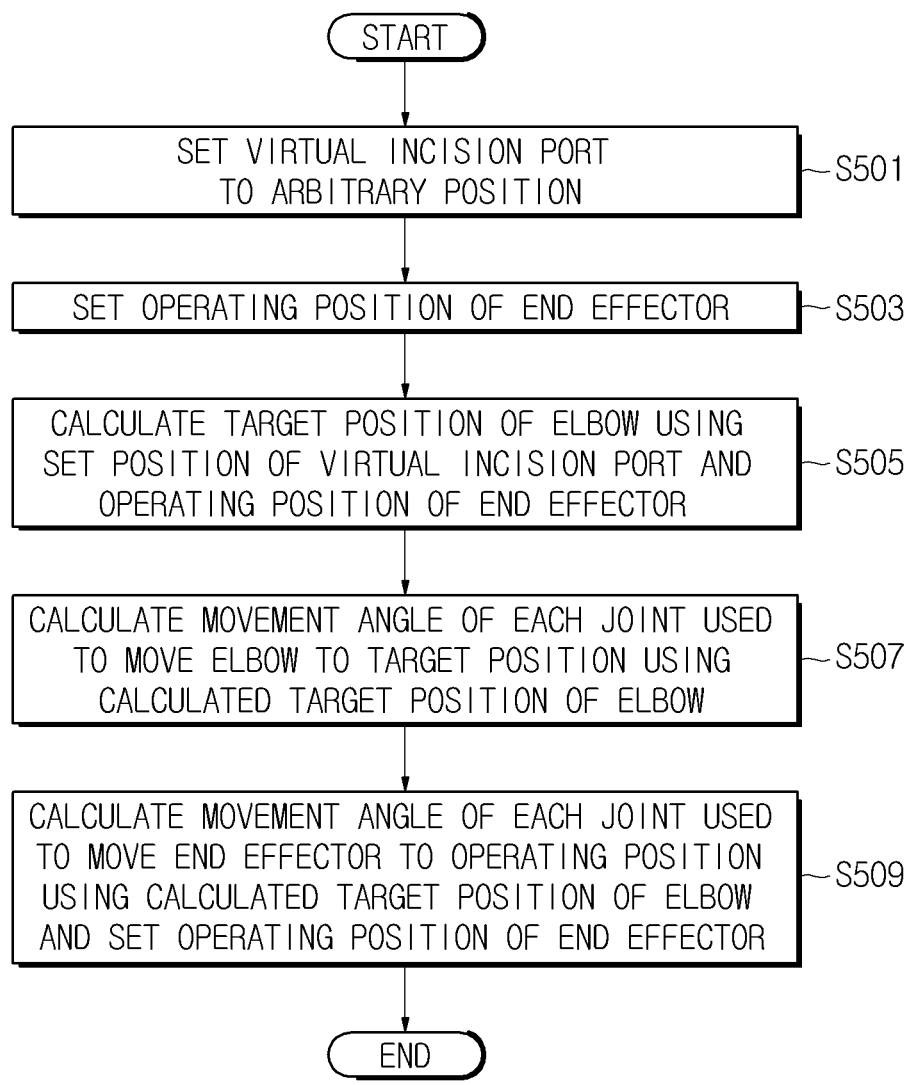
FIG. 5 is a flowchart showing the sequence of a control method of a single-port surgical robot according to some example embodiments.

FIG. 5 is a flowchart showing the sequence of a control method of a single-port surgical robot according to some example embodiments.

First, as exemplarily shown in FIG. 5, a Virtual Incision Port (VIP) is set to an arbitrary position (operation S501). Here, the virtual incision port is not present in reality, and may be a virtual Remote Center of Motion (RCM). The "remote center of motion" means the virtual center of an incision (see FIG. 2), and the surgical instruments 220 inserted into the incision may be controlled to move only within a conical workspace, an apex of which is the remote center of motion. That is, as exemplarily shown in FIG. 2, under coincidence of the remote center of motion and the patient's incision, the surgical instruments 220 inserted into the patient's body are moved only within the conical workspace even if any movement occurs at the robot arms located outside the incision. This may prevent the incision into which the surgical instruments have been inserted from being damaged due to movement of the robot arms.

Figure 6:
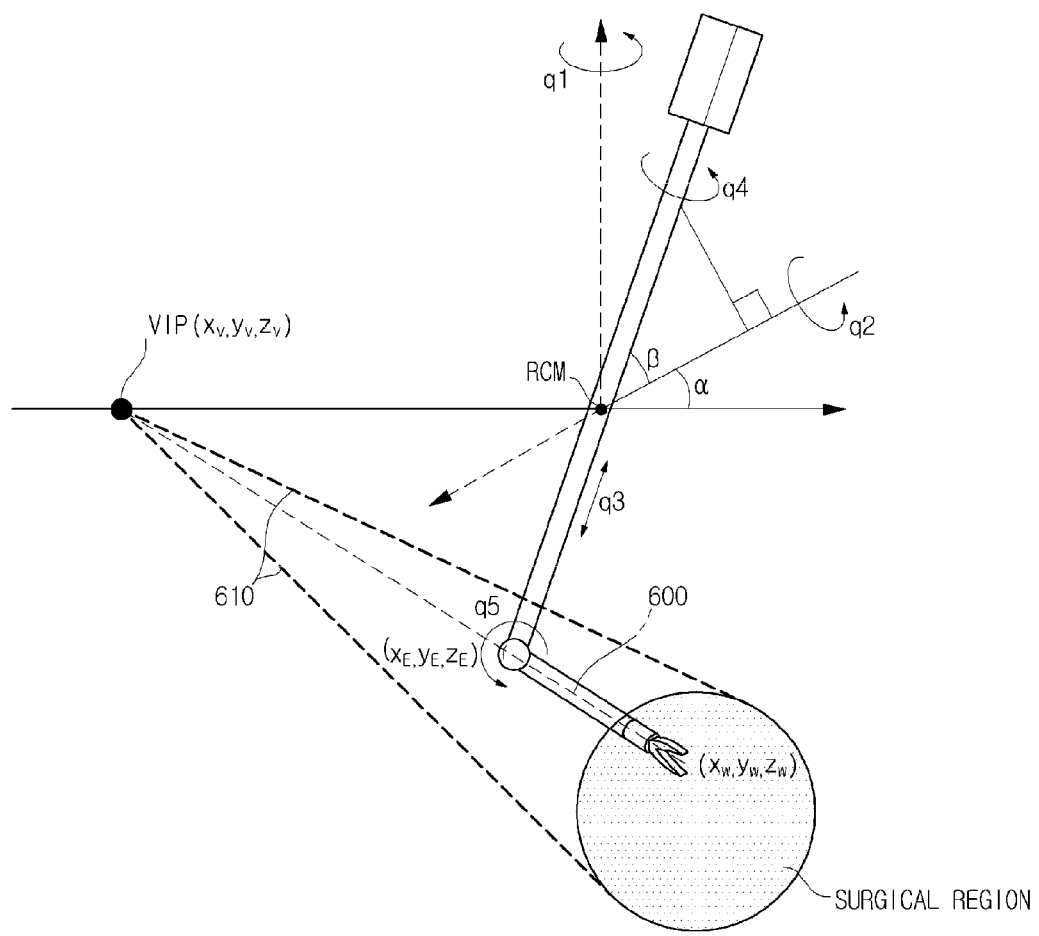
FIG. 6 is a view showing elbow position calculation using a virtual incision port.

As exemplarily shown in FIG. 6, the position of the virtual incision port may be one point $(x_V, y_V, z_V)$ in 3D coordinates. Although the position of the virtual incision port may be set by the following methods in some example embodiments, setting of the position of the virtual incision port is not in any way limited thereto.

In a first method, the operator may intuitively set a position of the virtual incision port based on experience.

In a second method, the virtual incision port may be set to a position using a movable angular range of each joint of the robot arm 210. In this method, each joint of the robot arm 210 may be initially moved to a middle value of a movable angle, and thereafter a position of the virtual incision port at a corresponding point may be acquired. More specifically, since the movement angle of each joint is known, an operating position of the end effector 225 and a target position of the elbow 223 may be calculated by subjecting the movement angle of each joint to forward kinematics. In addition, a length from the end effector 225 to the elbow 223 and a length from the elbow 223 to the virtual incision port are constant parameters (that may or may not be predetermined). As such, the position of the virtual incision port may be acquired by substituting the calculated operating position of the end effector 225, the calculated target position of the elbow 223, the length from the end effector 225 to the elbow 223, and the length from the elbow 223 to the virtual incision port into the following Equation 1 and Equation 2.

$$\vec{RV} = \vec{RW} + \vec{WV} \quad \text{Equation 1}$$

$$\vec{WV} = \frac{\vec{RE} - \vec{RW}}{|\vec{RE} - \vec{RW}|}(|\vec{WE}| + |\vec{EV}|) \quad \text{Equation 2}$$

Figure 7:
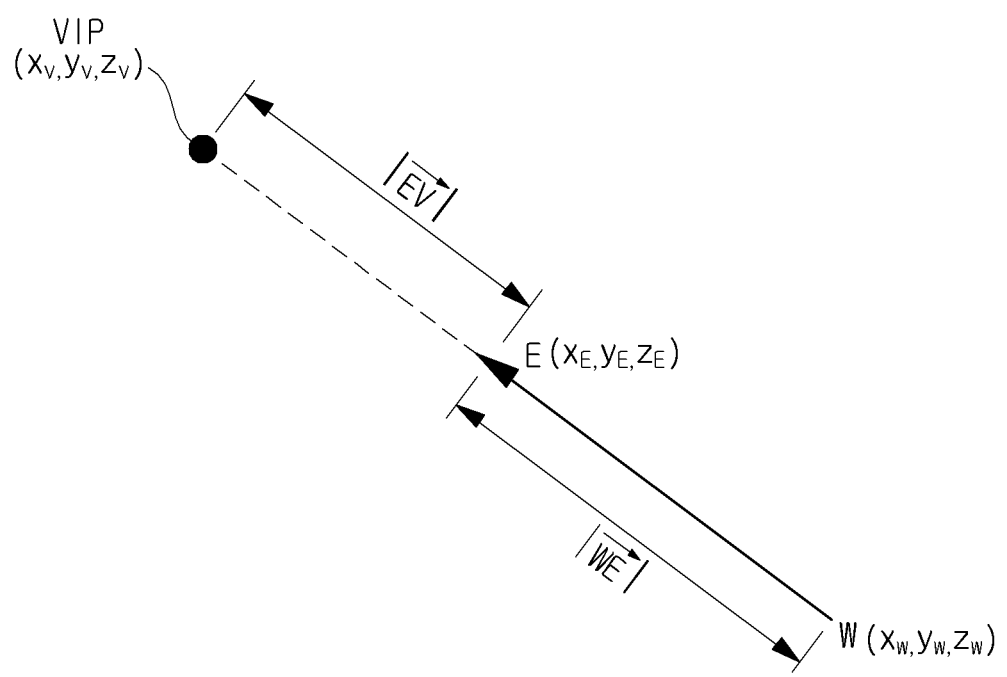
FIG. 7 is a view showing virtual incision port position calculation using an operating position of an end effector and a target position of an elbow.

Here, 'R' denotes a real incision port position, 'V' denotes a virtual incision port position, 'E' denotes an elbow target position, and 'W' denotes an end effector operating position. In this case, the length $|\vec{WE}|$ from the end effector 225 to the elbow 223 and the length $|\vec{EV}|$ from the elbow 223 to the virtual incision port may be previously given as constant parameters (see FIG. 7).

Next, an operating position of the end effector 225 is set (operation S503).

In this case, an operating position of the end effector 225 may be set according to a control signal received from the master device 100. That is, as the operator manipulates the input unit 110 of the master device 100, a control signal corresponding to an operating position of the end effector 225 that the operator desires may be generated and transmitted from the master device 100 to the slave device 200. Here, the "operating position" may mean a real action position of the end effector 225 that the operator desires. In addition, the operating position of the end effector 225 may be one point ($x_W$, $y_W$, $z_W$) in 3D coordinates (see FIG. 6) like the aforementioned virtual incision port.

Next, a target position of the elbow 223 is calculated using the set position of the virtual incision port and the set operating position of the end effector 225 (operation S505). Here, it may be necessary for the elbow 223 to reach the "target position", in order to ensure that the end effector 225 is moved to the operating position.

In this case, calculation of the target position of the elbow 223 as exemplarily shown in FIG. 6 may be implemented in such a way that the target position of the elbow 223 is positioned in a straight line 600 that connects the position of the virtual incision port and the operating position of the end effector 225 to each other. As such, the position of the virtual incision port, the target position of the elbow 223, and the operating position of the end effector 225 are arranged in a straight line as if the operator were inserting a straight surgical instrument through the virtual incision port. Accordingly, the operator may intuitively manipulate the surgical instrument 220 that is bent about the elbow 223 as if the operator were manipulating a straight surgical instrument. Additionally, situations in which end effector 225 cannot be moved to the correct operating position due to the presence of other robot arms 210 and/or other end effectors 225 may be avoided.

In addition, as described above, by determining the target position of the elbow 223 so as to be positioned in the straight line 600 that connects the position of the virtual incision port and the operating position of the end effector 225 to each other, it may be possible to ensure that the elbow 223 is included in a guaranteed range 610 as exemplarily shown in FIG. 6, which may prevent damage to internal organs, surrounding tissues, and the like due to movement of the elbow 223. Here, the "guaranteed range" may mean a range in which the elbow 223 is movable without causing damage to the surrounding organs, tissues, and the like.

In this case, the target position of the elbow 223 may be calculated using the following Equation 3 and Equation 4.

$$\vec{RE} = \vec{RW} + \vec{WE} \quad \text{Equation 3}$$

$$\vec{WE} = \frac{\vec{RV} - \vec{RW}}{|\vec{RV} - \vec{RW}|}|\vec{WE}| \quad \text{Equation 4}$$

Here, 'R' denotes a real incision port position, 'V' denotes a set virtual incision port position, 'E' denotes a calculated elbow target position, and 'W' denotes a set end effector operating position. In this case, the length $|\vec{WE}|$ from the end effector 225 to the elbow 223 may be previously given as a constant parameter. The target position of the elbow 223 calculated via the aforementioned Equation 3 and Equation 4 may be one point ($x_E$, $y_E$, $z_E$) in 3D coordinates (see FIG. 6).

Next, a movement angle of each joint to move the elbow 223 to the target position is calculated using the calculated target position of the elbow 223 (operation S507). In this case, calculation of the movement angle of each joint may be implemented by subjecting the calculated target position of the elbow 223 to inverse kinematics, without being in any way limited thereto. Here, a method to acquire a solution using inverse kinematics is known and, thus, a detailed description thereof will be omitted herein. Through implementation of the above calculation, movement angles q1, q2, and q3 of first to third joints (see FIG. 6) to move the elbow 223 to the target position may be calculated.

Next, movement angles q4 and q5 of fourth and fifth joints (see FIG. 6) to move the end effector 225 to the operating position are calculated using the calculated target position of the elbow 223 and the set operating position of the end effector 225 (operation S509). In this case, calculation of the movement angles of the respective joints may be implemented by subjecting the calculated target position of the elbow 223 and the set operating position of the end effector 225 to inverse kinematics as described above, without being in any way limited thereto.

As such, in some example embodiments, setting the virtual incision port to a position and positioning the target position of the elbow 223 in a straight line that connects the set position of the virtual incision port and the operating position of the end effector 225 set by the operator to each other may realize a state as if the operator were inserting a straight surgical instrument through the virtual incision port. As such, the bent surgical instrument of some example embodiments may have the same function as that of a straight surgical instrument used in a multi-port surgical robot. Thus, the operator may manipulate the bent surgical instrument 220 with the same sensation as performing surgery using the straight surgical instrument of the multi-port surgical robot, which may assist quick adaptation of operators who use a conventional multi-port surgical robot.

Although the single robot arm 210 has been described above, this is given for convenience of description, and the disclosure is not limited thereto and it will be clearly understood that the disclosure may be applied to two or more robot arms 210. In the case of a plurality of robot arms 210, a virtual incision port may be set on a per robot arm basis, or the plurality of robot arms 210 may commonly use one virtual incision port.

In addition, the position of the aforementioned virtual incision port may be fixed, but may be dynamically changed. Hereinafter, a control method using the virtual incision port, a position of which is dynamically changeable, will be described.

Figure 8:
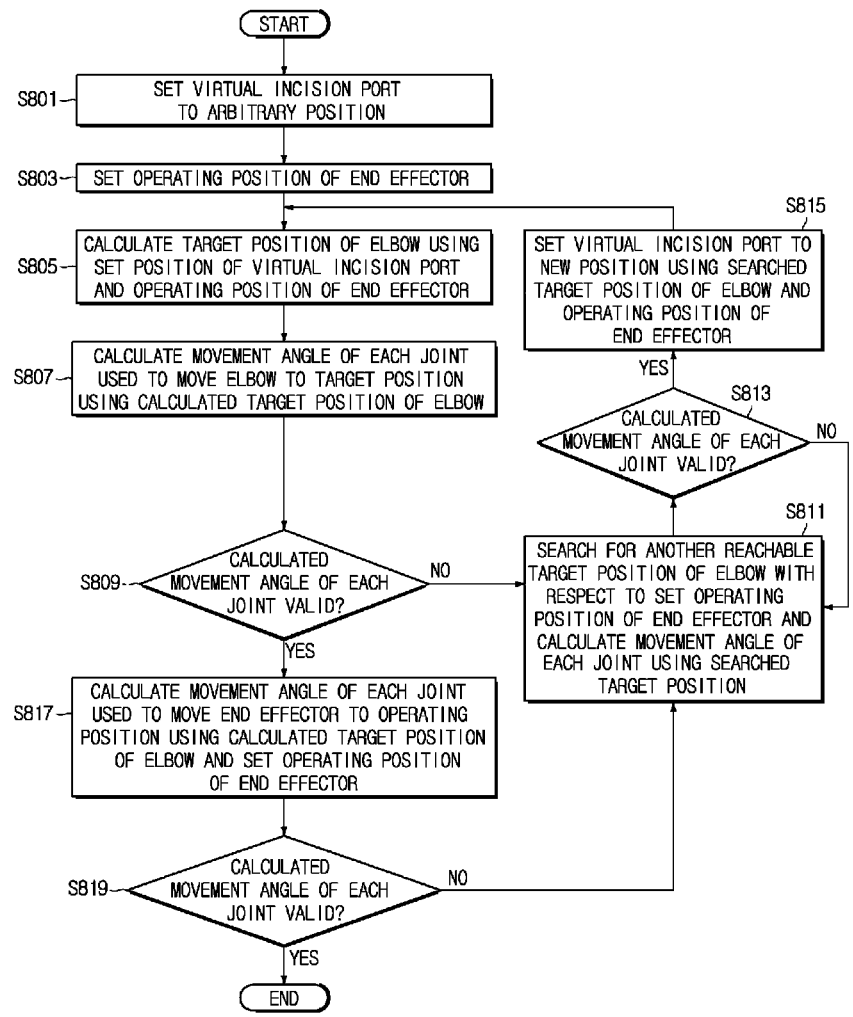
FIG. 8 is a flowchart showing the sequence of a control method of a single-port surgical robot according to some example embodiments.

FIG. 8 is a flowchart showing the sequence of a control method of a single-port surgical robot according to some example embodiments. Hereinafter, a repeated description of the above-described embodiments may be omitted.

After a virtual incision port is set to an arbitrary position (operation S801) and an operating position of the end effector 225 is set (operation S803), a target position of the elbow 223 is calculated using the set position of the virtual incision port and the operating position of the end effector 225 (operation S805). In this case, the target position of the elbow 223 may be calculated using the aforementioned Equation 3 and Equation 4.

Next, movement angles q1, q2, and q3 of first to third joints (see FIG. 6) to move the elbow 223 to the target position may be calculated by subjecting the calculated target position of the elbow 223 to inverse kinematics (operation S807).

Thereafter, it is judged whether or not the calculated movement angles q1, q2, and q3 of the respective joints are valid (operation S809). In this case, validity of the movement angles q1, q2, and q3 of the respective joints may be judged based on whether or not the movement angles q1, q2, and q3 are respectively included in a movable angular range of the first joint, a movable angular range of the second joint, and a movable angular range of the third joint.

If the judged result shows that the movement angles q1, q2, and q3 are not included in the respective movable angular ranges of the first, second, and third joints and, thus, are not valid, another reachable target position of the elbow 223 is searched with respect to the set operating position of the end effector 225. Then, movement angles q1, q2, and q3 of the first, second, and third joints are recalculated using the searched target position of the elbow 223 (operation S811). In this case, search for another reachable target position of the elbow 223 with respect to the set operating position of the end effector 225 may include searching for positions of all points included in a surface of a sphere, a radius of which is a length from the end effector 225 to the elbow 223.

Figure 9:
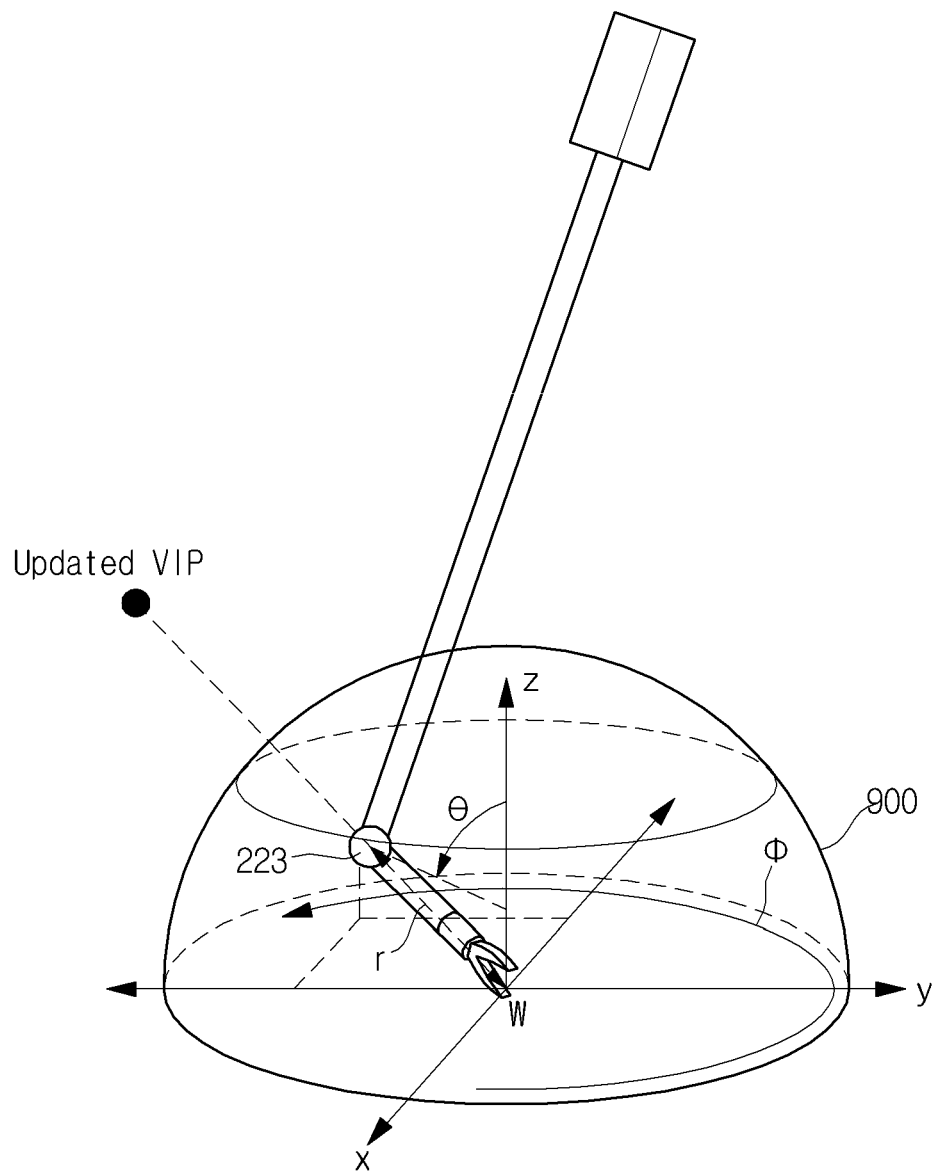
FIG. 9 is a view showing investigation of a reachable target position of an elbow with respect to an operating position of an end effector.

Referring to FIG. 9, since a length 'r' from the end effector 225 to the elbow 223 is previously given and an operating position of the end effector 225 may be a desired location (that may or may not be predetermined), a surface 900 of a sphere about the end effector 225, a radius of which is the length 'r' from the end effector 225 to the elbow 223, corresponds to the entire set of reachable target positions of the elbow 223. As such, another reachable target position of the elbow 223 may be searched by changing 'θ' and 'ϕ' in a state in which the length from the end effector 225 to the elbow 223 is fixed in polar coordinates as exemplarily shown in FIG. 9.

Although another reachable target position of the elbow 223 may be searched by the aforementioned method, alternatively, various target positions of the elbow 223 with respect to the set operating position of the end effector 225 may be selected using a 3D Look-Up Table (LUT) in which a target position of the elbow 223 that ensures calculation of valid movement angles of joints is selected from among a plurality of target positions of the elbow 223 with respect to the operating position of the end effector 225 and is matched to the corresponding operating position of the end effector 225.

More specifically, all possible operating positions of the end effector 225 are acquired by subjecting movable angular ranges of joints for motion control of the end effector 225, i.e., movable angular ranges of the first, second, third, fourth, and fifth joints to forward kinematics. Thereafter, all reachable target positions of the elbow 223 with respect to all of the acquired operating positions of the end effector 225 are searched, and movement angles q1, q2, q3, q4, and q5 of the respective joints are acquired by subjecting all of the searched target positions of the elbow 223 to inverse kinematics. Then, only target positions of the elbow 223 based on valid movement angles are matched to the corresponding operating position of the end effector 225 and are stored in the 3D LUT.

Next, whether or not the recalculated movement angles q1, q2, and q3 of the first, second, and third joints are valid is judged (operation S813). If the movement angles q1, q2, and q3 are not valid, the method returns to operation S811 to search for another reachable target position of the elbow 223 (or to select another target position of the elbow 223 from the LUT) and to recalculate the movement angles q1, q2, and q3 of the first, second, and third joints using the searched (or selected) target position of the elbow 223. Operations S811 and S813 may be repeated until all of the calculated movement angles are judged valid.

Thereafter, if all of the movement angles are valid, the virtual incision port is set to a new position using the corresponding target position of the elbow 223 and the set operating position of the end effector 225 (operation S815). In this case, the new position of the virtual incision port may be acquired using the aforementioned Equation 1 and Equation 2.

Then, a target position of the elbow 223 is calculated using the newly set position of the virtual incision port and the set operating position of the end effector 225 (operation S805), the movement angles of the corresponding joints are calculated using the calculated target position of the elbow 223 (operation S807), and whether or not the calculated movement angles of the respective joints are valid is judged (operation S809). If the calculated movement angles of the respective joints are not valid, another reachable target position of the elbow 223 is repeatedly searched (or another target position of the elbow 223 is selected from the LUT), and the movement angles q1, q2, and q3 of the first, second, and third joints are repeatedly calculated using the searched (or selected) target position of the elbow 223 (operation S811).

If the judged result shows that all of the movement angles are valid, movement angles q4 and q5 of the fourth and fifth joints (see FIG. 6) to move the end effector 225 to the operating position are calculated by subjecting the calculated target position of the elbow 223 or the newly searched target position of the elbow 223 as well as the set operating position of the end effector 225 to inverse kinematics (operation S817).

Thereafter, whether or not the calculated movement angles q4 and q5 of the fourth and fifth joints are valid is judged (operation S819). Likewise, validity may be judged based on whether or not the movement angles q4 and q5 are included within movable angular ranges of the fourth and fifth joints. If the judged result shows that the movement angles q4 and q5 are not valid, another reachable target position of the elbow 223 is repeatedly searched or (another target position of the elbow 223 is selected from the LUT), and the movement angles q1, q2, and q3 of the first, second, and third joints are recalculated using the searched (or selected) target position of the elbow 223 (operation S811). Thereafter, whether or not the recalculated movement angles are valid is judged (operation S813). If the movement angles are valid, the virtual incision port is set to a new position using the searched target position of the elbow 223 and the operating position of the end effector 225 (operation S815). Thereafter, a target position of the elbow 223 is calculated using the newly set position of the virtual incision port and the set operating position of the end effector 225 (operation S805). These operations may be repeated until all of the calculated movement angles of the respective joints are judged valid.

Meanwhile, in the aforementioned operation S815 of setting the virtual incision port to a new position, the length from the elbow 223 to the virtual incision port may be previously given. That is, the length from the elbow 223 to the virtual incision port may be adjusted such that the virtual incision port is located inside or outside the abdominal cavity of the patient P. In this case, a movement range of the elbow 223 may be changed based on whether the virtual incision port is located inside or outside the abdominal cavity. The ability to locate the virtual incision port inside or outside the abdominal cavity of the patient P significantly increase flexibility in the manipulation of the surgical robot and robot arms 210.

Figure 10:
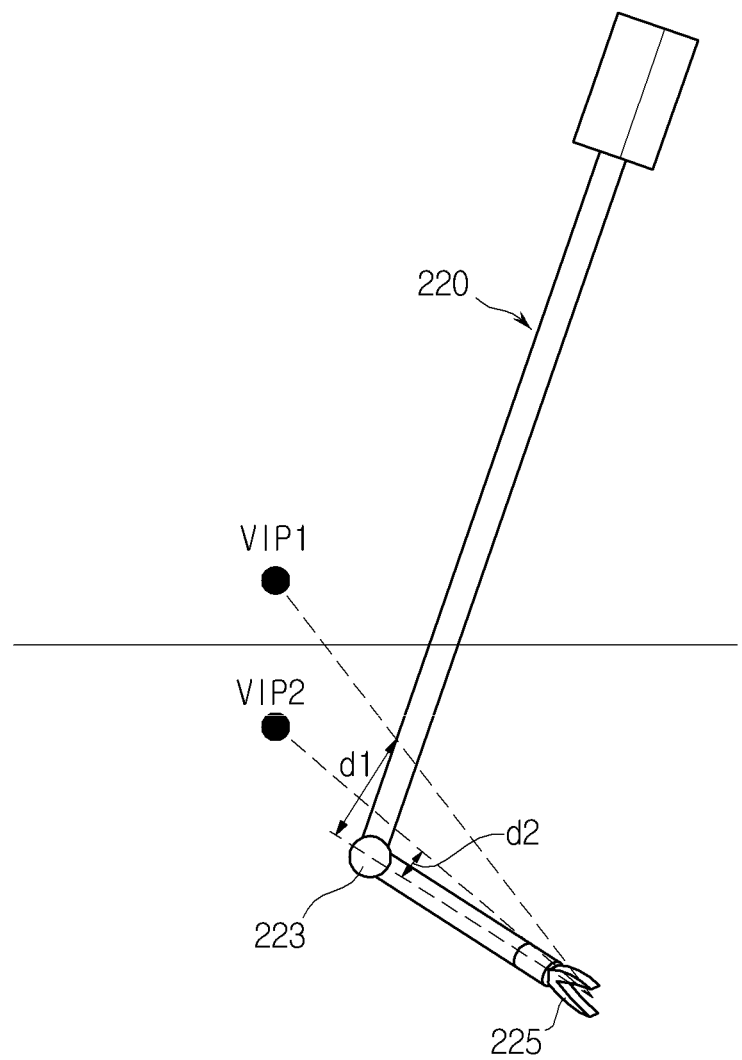
FIG. 10 is a view showing the movement range of an elbow in both cases in which a virtual incision port is located outside and inside the patient's body.

That is, whenever the position of the virtual incision port is changed, it may be necessary to move the elbow 223 so as to be located in a straight line that connects the virtual incision port and the end effector 225 to each other. As exemplarily shown in FIG. 10, comparing the case in which the virtual incision port is located outside the abdominal cavity (VIP1) with the case in which the virtual incision port is located inside the abdominal cavity (VIP2), a movement distance d1 of the elbow 223 in the case of the virtual incision port inside the abdominal cavity (VIP2) is shorter than a movement distance d2 of the elbow 223 in the case of the virtual incision port outside the abdominal cavity (VIP1). That is, the movement range of the elbow 223 is reduced when the virtual incision port is located inside the abdominal cavity. The reduced movement range of the elbow 223 may ensure easier motion of the surgical instrument 220 in a narrow workspace within the body of the patient P and may prevent the organs or surrounding tissues within the body of the patient P from being damaged due to movement of the surgical instrument 220.

The aforementioned control method of the single-port surgical robot may be stored in a recording medium so as to be implemented in conjunction with a desired apparatus (that may or may not be predetermined), for example, a single-port surgical robot system. Here, the "recording medium" may be a magnetic or optical recording medium, such as a hard disk, video tape, compact disc (CD), video CD (VCD), digital video disc (DVD), etc., or a database of a client or server computer built in an online manner, without being in any way limited thereto.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A control method of a single-port surgical robot, the single-port surgical robot including a slave device including a surgical instrument having a proximal end and a distal end, the distal end including an elbow and an end effector, and a master device to control motion of the slave device, the method comprising:
    setting a virtual incision port to an arbitrary position;
    setting an operating position of the end effector;
    calculating a target position of the elbow using a position of the virtual incision port and the set operating position of the end effector;
    calculating a first movement angle of each joint used to move the elbow using the calculated target position of the elbow; and
    calculating a second movement angle of each joint used to move the end effector using the calculated target position of the elbow and the set operating position of the end effector,
    wherein the calculating of the target position of the elbow calculates the target position of the elbow such that the target position of the elbow is positioned in a straight line that connects the position of the virtual incision port and the set operating position of the end effector to each other with the elbow being bent at an elbow angle such that the straight line does not pass through the proximal end of the surgical instrument.

2. The method according to claim 1, wherein the calculating of the target position of the elbow is implemented using the following equations:

$$\vec{RE} = \vec{RW} + \vec{WE}$$

$$\vec{WE} = \frac{\vec{RV} - \vec{RW}}{|\vec{RV} - \vec{RW}|}|\vec{WE}|$$

wherein 'R' denotes a real incision port position, 'V' denotes a virtual incision port position, 'E' denotes an elbow target position, and denotes an end effector operating position.

3. The method according to claim 1, wherein the setting of the operating position of the end effector is implemented upon receiving a control signal from the master device.

4. The method according to claim 1, wherein the setting of the virtual incision port is implemented in such a way that the position of the virtual incision port is located at a surface of a body of a patient, outside an abdominal cavity of the patient, or inside the abdominal cavity of the patient.

5. The method according to claim 1, further comprising, after the calculating of the first movement angle of each joint used to move the elbow, judging whether or not the calculated first movement angle of each joint is valid.

6. The method according to claim 5, wherein judgment of whether or not the first movement angle of each joint is valid is implemented by judging whether or not the first movement angle of each joint is included within a movable angular range of the corresponding joint.

7. The method according to claim 5, wherein after judgment of whether or not the first movement angle of each joint is valid, the calculating of the second movement angle of each joint used to move the end effector using the calculated target position of the elbow and the operating position of the end effector is implemented if the first movement angle of each joint is valid.

8. The method according to claim 5, further comprising, after judgment of whether or not the first movement angle of each joint is valid:
searching for another reachable target position of the elbow with respect to the set operating position of the end effector if the first movement angle of each joint is not valid;
recalculating the first movement angle of each joint used to move the elbow using the searched target position of the elbow; and
judging whether or not the recalculated first movement angle of each joint is valid.

9. The method according to claim 8, wherein the searching for the another reachable target position of the elbow is implemented using a set of all points included in a surface of a sphere about the set operating position of the end effector, a radius of the sphere being a length from the end effector to the elbow.

10. The method according to claim 8, wherein the searching for the another reachable target position of the elbow is implemented using a three-dimensional (3D) look-up table in which a valid target position of the elbow, among reachable target positions of the elbow with respect to the set operating position of the end effector, is matched to a corresponding operating position of the end effector.

11. The method according to claim 8, further comprising, after the judging of whether or not the recalculated first movement angle of each joint is valid, setting the virtual incision port to a new position using the searched target position of the elbow and the set operating position of the end effector if the recalculated first movement angle of each joint is valid.

12. The method according to claim 11, wherein after the setting of the new position of the virtual incision port, calculating of the target position of the elbow using the newly set position of the virtual incision port and the set operating position of the end effector is implemented.

13. The method according to claim 11, wherein the setting of the position of the virtual incision port is implemented using the following equations:

$$\overrightarrow{RV} = \overrightarrow{RW} + \overrightarrow{WV}$$

$$\overrightarrow{WV} = \frac{\overrightarrow{RE} - \overrightarrow{RW}}{|\overrightarrow{RE} - \overrightarrow{RW}|}(|\overrightarrow{WE}| + |\overrightarrow{EV}|)$$

wherein 'R' denotes a real incision port position, 'V' denotes a virtual incision port position, 'E' denotes an elbow target position, and 'W' denotes an end effector operating position.

14. The method according to claim 8, wherein after the judging of whether or not the recalculated first movement angle of each joint is valid, searching for the another reachable target position of the elbow and the recalculating of the first movement angle of each joint used to move the elbow using the another reachable target position of the elbow are repeatedly implemented if the recalculated first movement angle of each joint is not valid.

15. The method according to claim 1, further comprising, after the calculating of the second movement angle of each joint used to move the end effector, judging whether or not the calculated second movement angle of each joint is valid.

16. The method according to claim 15, wherein after the judging of whether or not the second movement angle of each joint is valid, searching for another reachable target position of the elbow with respect to the set operating position of the end effector, recalculating of the first movement angle of each joint used to move the elbow using the searched target position of the elbow, and the judging of whether or not the recalculated first movement angle of each joint is valid are repeatedly implemented if the second movement angle of each joint is not valid.

17. The method according to claim 16, wherein the searching for the another reachable target position of the elbow is implemented using a set of all points included in a surface of a sphere about the set operating position of the end effector, a radius of the sphere being a length from the end effector to the elbow.

18. The method according to claim 16, wherein after the judging of whether or not the recalculated first movement angle of each joint is valid, setting of a new position of the virtual incision port using the searched target position of the elbow and the set operating position of the end effector is implemented if the recalculated first movement angle of each joint is valid.

19. The method according to claim 16, wherein after the judging of whether or not the recalculated first movement angle of each joint is valid, the searching for the another reachable target position of the elbow and recalculation of the first movement angle of each joint used to move the elbow using the searched target position of the elbow are repeatedly implemented if the recalculated first movement angle of each joint is not valid.

* * * * *